US012303636B2

(12) United States Patent
Burban et al.

(10) Patent No.: US 12,303,636 B2
(45) Date of Patent: May 20, 2025

(54) SYSTEM FOR GRAVITY INCLUSION OF POWDER INTO A MEDICAL DELIVERY FLOW STREAM

(71) Applicants: John H. Burban, Lake Elmo, MN (US); John W. Shanahan, White Bear Lake, MN (US); Michael R. Spearman, The Woodlands, TX (US); Craig J. Cuta, Stillwater, MN (US); Keith A. Roberts, Dellwood, MN (US)

(72) Inventors: John H. Burban, Lake Elmo, MN (US); John W. Shanahan, White Bear Lake, MN (US); Michael R. Spearman, The Woodlands, TX (US); Craig J. Cuta, Stillwater, MN (US); Keith A. Roberts, Dellwood, MN (US)

( * ) Notice: Subject to any disclaimer, the term of this patent is extended or adjusted under 35 U.S.C. 154(b) by 727 days.

(21) Appl. No.: 17/241,616

(22) Filed: Apr. 27, 2021

(65) Prior Publication Data

US 2021/0330902 A1    Oct. 28, 2021

Related U.S. Application Data

(60) Provisional application No. 63/014,671, filed on Apr. 23, 2020.

(51) Int. Cl.
*A61M 13/00* (2006.01)
*A61M 39/22* (2006.01)

(52) U.S. Cl.
CPC ....... *A61M 13/00* (2013.01); *A61M 2039/229* (2013.01); *A61M 2202/064* (2013.01)

(58) Field of Classification Search
CPC ............ A61M 13/00; A61M 2039/229; A61M 2202/064; A61M 15/0066; A61B 2017/00522; A61B 17/00491
See application file for complete search history.

(56) References Cited

U.S. PATENT DOCUMENTS

| | | | |
|---|---|---|---|
| 10,441,761 B2 | 10/2019 | Christakis et al. | |
| 11,701,448 B2 | 7/2023 | Smith et al. | |
| 11,931,003 B2 | 3/2024 | Congdon et al. | |
| 2011/0178495 A1* | 7/2011 | Ji | A61M 15/0016 606/213 |
| 2011/0251580 A1* | 10/2011 | Greenhalgh | A61M 35/003 604/500 |
| 2018/0193574 A1* | 7/2018 | Smith | A61M 13/00 |
| 2019/0232030 A1* | 8/2019 | Pic | A61B 17/00491 |
| 2024/0108402 A1 | 4/2024 | Govari et al. | |

* cited by examiner

*Primary Examiner* — Nathan R Price
*Assistant Examiner* — Fatimata Sahra Diop
(74) *Attorney, Agent, or Firm* — Mark A. Litman & Associates, PA

(57) ABSTRACT

A method and apparatus deliver dry, flowable hemostatic powder into a gas flow stream by gravity delivery within a body of the apparatus. The hemostatic powder is then carried with the gas out of the apparatus into an elongated delivery tube inserted into a patient. Delivery of the powder into the gas flow stream creates a bolus of powder and air which becomes more uniformly distributed as it passes through the elongated delivery tube.

19 Claims, 5 Drawing Sheets

Figure 1:
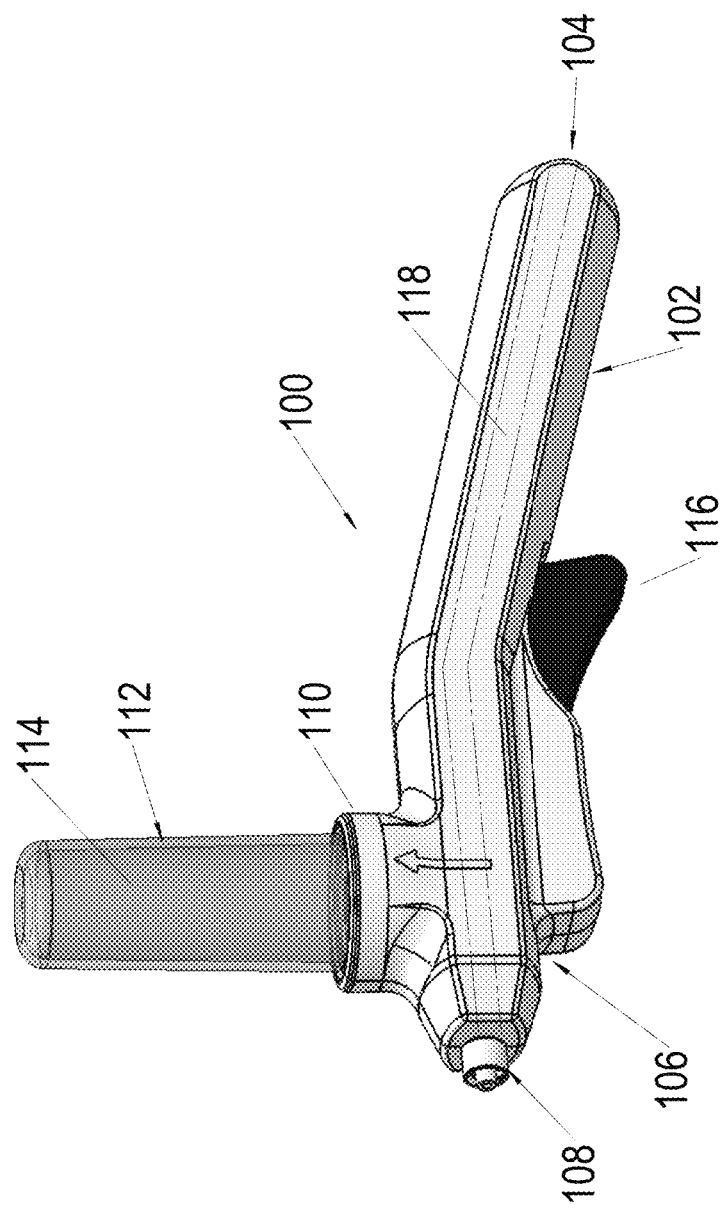
Figure 2:
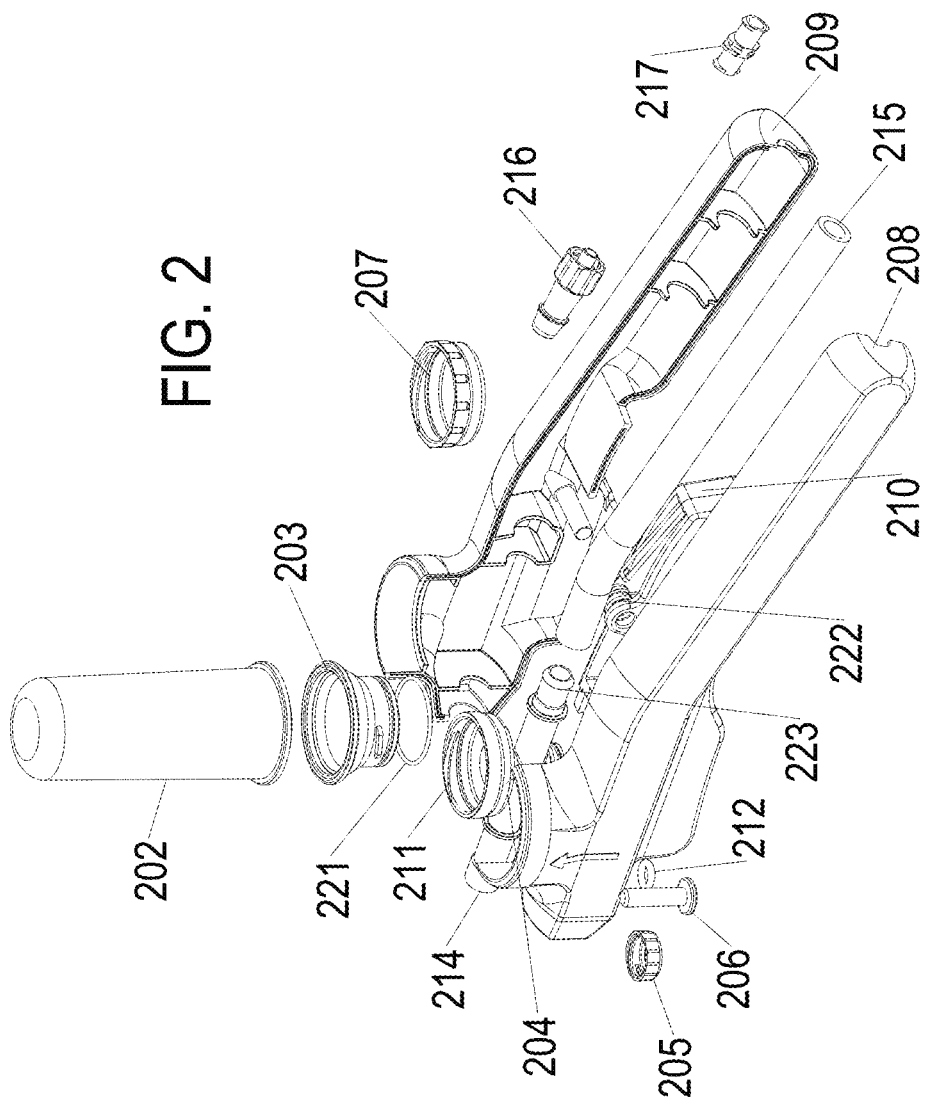
Figure 4:
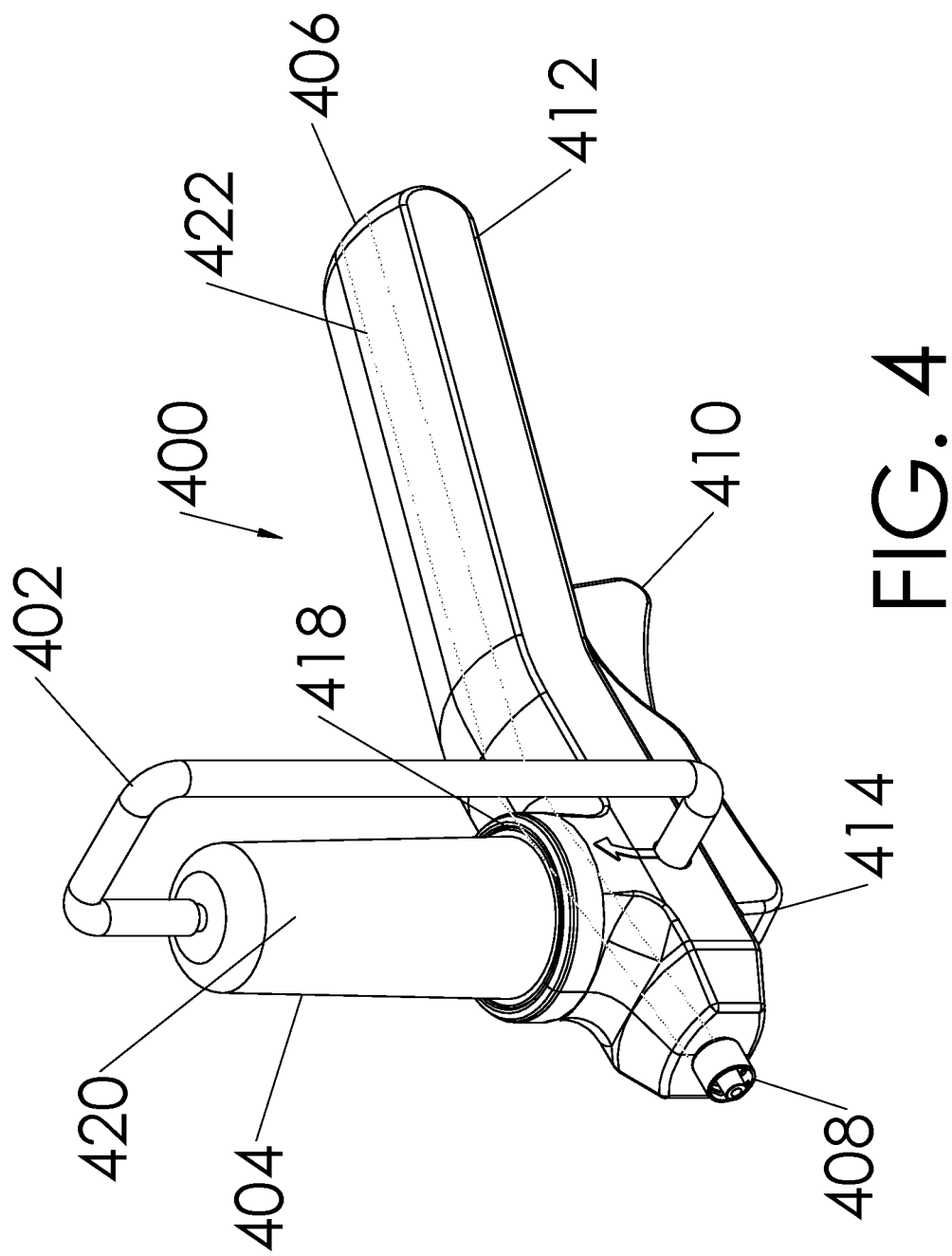
Figure 5:
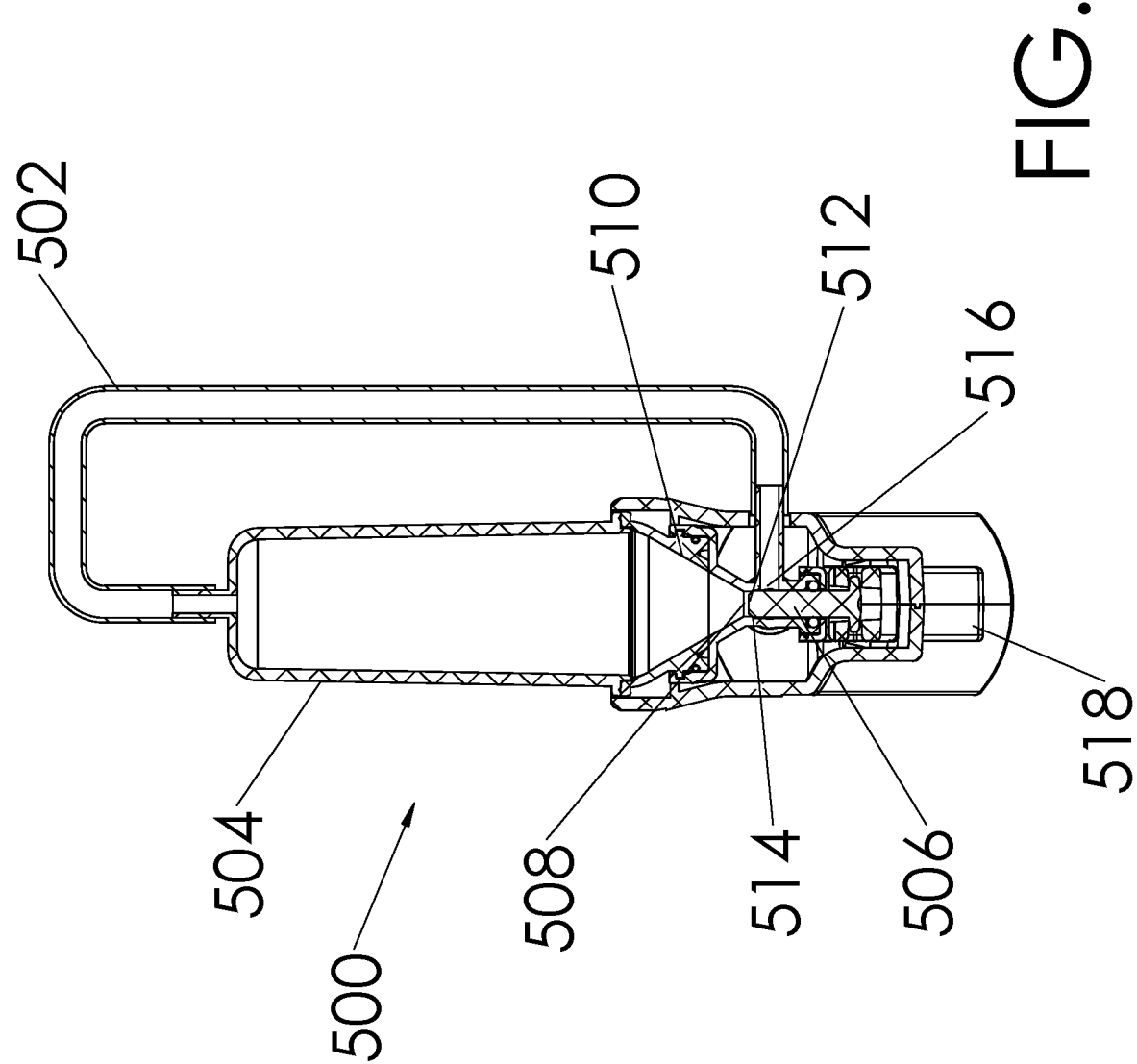

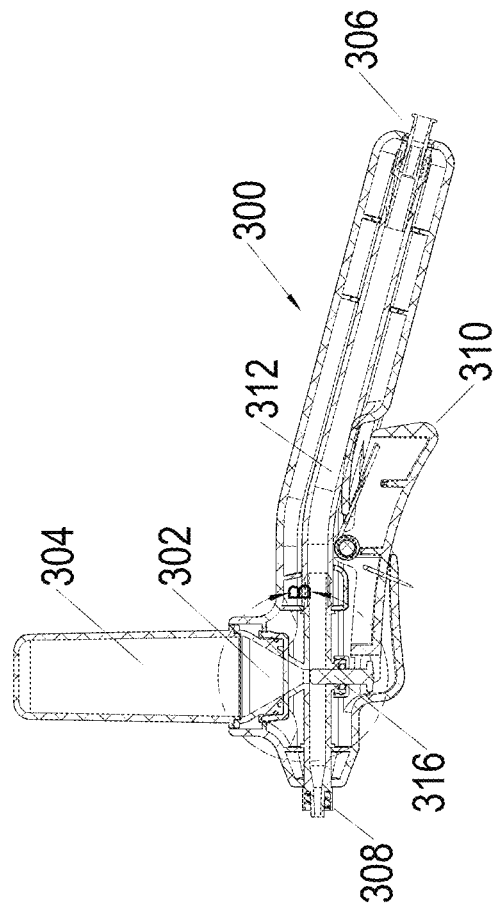
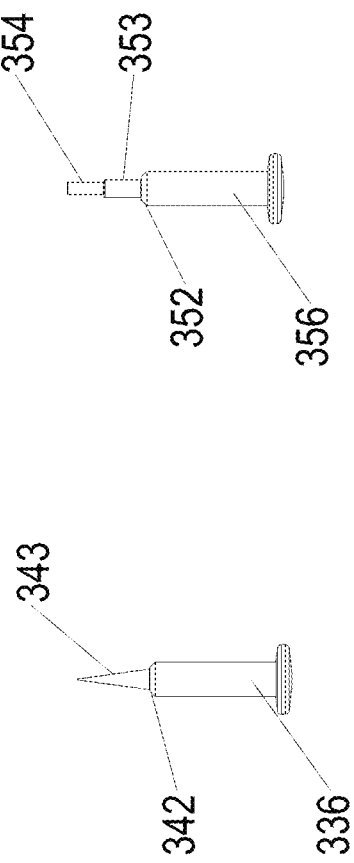
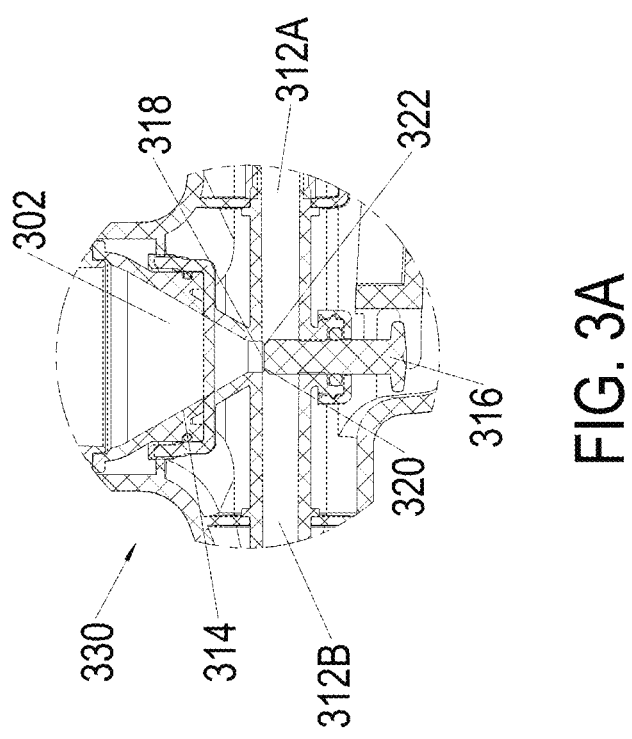
FIG. 3
FIG. 3A
FIG. 3B
FIG. 3C

SYSTEM FOR GRAVITY INCLUSION OF POWDER INTO A MEDICAL DELIVERY FLOW STREAM

RELATED APPLICATIONS DATA

This application claims priority from Provisional U.S. Patent application Ser. No. 63/014,671, filed 23 Apr. 2020. That application is incorporated by reference in its entirety.

BACKGROUND OF THE INVENTION

1. Field of the Invention

The present invention relates to the field of powder delivery, particularly dry powder delivery, and more particularly to dry powder delivery to internal patient sites. The powder may offer different medicinal benefits including but not limited to hemostasis, wound healing, localized medicine delivery, localized tissue response, and other interactions with the tissue the powder interacts with.

2. BACKGROUND OF THE ART

Internal tissue may bleed during a non-invasive surgical procedure or from disease on internal tissues. These situations make blood loss and visibility (during surgery) important concerns. During some procedures, a hemostatic agent may be applied to the affected bodily tissue to stop the bleeding, at least until a more robust method can be used to permanently stop the bleeding. These agents are often delivered as dry hemostatic powders. Many of these powders are known to agglomerate, or have agglomerative properties, making it more difficult to propel the powder through a lumen of an endoscope for delivery to a treatment site inside the body. For example, the lumen may become blocked by the material, especially if there is liquid within the lumen. As a result, some effective hemostatic agents may have disadvantages, for example, by requiring continuous delivery. Some of these powders are described in U.S. Pat. Nos. 6,992,233; 9,598,504; and 10,137,219 (Drake); and U.S. Pat. No. 8,703,176 (Zhu).

U.S. Pat. No. 9,629,966 (Ji) discloses an internal dry powder delivery system through a working channel of an endoscopic cannula for directly applying the powder form medication to an internal tissue/organ site. The system includes an elongated tubular delivery channel and a powder supply device for producing pressurized gas mixing with the dry powder for feeding to form a mixture of dry powder and pressurized gas delivering to an internal tissue/organ site through the delivery channel via endoscopic cannula. The system is asserted to ensure a smooth powder release by preventing liquid from accumulation at the tip of the delivery channel and offers physicians a new powder form drug delivery method via endoscope. Also, it offers new minimal invasive application by directly and precisely applying the powder format drug to the internal sites of human gastrointestinal organ via endoscope to achieve hemostasis, anti-inflammation, anti-ulcer and anti-tumor treatment, etc. Powder is injected by manually increasing pressure in the powder containing elements to eject powder into the delivery channel.

U.S. Pat. Nos. 9,205,207; 8,827,980; and 8,721,582 (Ji) disclose an internal dry powder delivery system through a working channel of an endoscopic cannula for directly applying the powder form medication to an internal tissue/organ site. The system includes an elongated tubular delivery channel and a powder supply device for producing pressurized gas mixing with the dry powder for feeding to form a mixture of dry powder and pressurized gas delivering to an internal tissue/organ site through the delivery channel via endoscopic cannula. The system is asserted to ensure a smooth powder release by preventing liquid from accumulation at the tip of the delivery channel and offers physicians a new powder form drug delivery method via endoscope. Also, it offers new minimal invasive application by directly and precisely applying the powder format drug to the internal sites of human gastrointestinal organ via endoscope to achieve hemostasis, anti-inflammation, anti-ulcer and anti-tumor treatment, etc. The system of this patent displayed technical issues addressed by U.S. Pat. No. 9,629,966

U.S. Pat. No. 8,118,777 (Ducharme) provides systems and methods suitable for delivering a therapeutic agent to a target site. The systems generally comprise a container for holding a therapeutic agent, and a pressure source configured to be placed in selective fluid communication with at least a portion of a reservoir of the container. In one embodiment, fluid from the pressure source is directed through a first region of the container in a direction towards a second region of the container. The fluid then is at least partially redirected to urge the therapeutic agent in a direction from the second region of the container towards the first region of the container and subsequently towards the target site. In alternative embodiments, the fluid from the pressure source may be directed through the second region of the container in a direction towards the first region of the container.

Published U.S. Patent Application Document No. 20180001067 (Christakis) disclosed implementations of a delivery device and method are disclosed. One implementation is a delivery device comprising a flow chamber with an inlet port for receiving a fluid flow in the flow chamber, and an outlet port for exiting a material from the flow chamber. The flow chamber may include a formation portion in which a suspension of the material is formed, and a collection portion that directs the suspension toward and/or into the outlet port. An amount of the material may collect in the collection portion adjacent the outlet port. The device may further comprise an insertion port for permitting insertion of the material in the flow chamber, and/or a pusher operable to move the amount of material through the outlet port. Related devices and methods also are disclosed. Pressure in the powder storage area is manually increased to eject powder into a flow stream.

Improved hemostatic powder delivery system to internal wounds and sores are needed. All documents cited herein are incorporated by reference in their entireties.

Published US Patent Document No. 20070286892 (Herzberg) discloses compositions and methods for preventing or reducing postoperative ileus and gastric stasis. Such compositions include a combination of a carrier component and a bioactive component which acts to prevent or reduce post-operative ileus. Such methods include administering a therapeutically effective amount of the composition directly to the serosal surfaces of the gastrointestinal and other visceral organs.

Although powder coating is an unrelated field of technology, the application of powders to surfaces, as in Published US Patent Application Document 20060097071 (Robideaux) should be considered.

SUMMARY OF THE INVENTION

A method and apparatus deliver dry, flowable medicinal powder into a gas flow stream by gravity delivery within a body of the apparatus. The medicinal powder is then carried with the gas out of the apparatus into an elongated delivery tube inserted into a patient. Delivery of the powder into the gas flow stream creates a bolus of powder and air which becomes more uniformly distributed as it passes through the elongated delivery tube.

While in this invention description, the preferred powder delivered to the patient is described as hemostatic, powders with other medicinal benefit can also be delivered to a patient with the same device. Other powders may include but are not limited to: mucoadhesive polymers, wound healing polymers, powders that act as neutralizing agents for the acidic gastric environment, proton pump inhibitors, powdered biologics, anti-microbial agents, etc. Powders may be delivered individually or as mixtures with any other powder as actives or as inert carrier. For the sake of clarity and brevity, the term hemostatic generally will be used to further describe the invention, however the invention can apply to any of the other medicinal powders as described above.

BRIEF DESCRIPTION OF THE FIGURES

FIG. 1 shows a perspective view of a hand-held hemostatic dry powder application device within the scope of the present invention.

FIG. 2 shows an exploded perspective view of a hand-held hemostatic dry powder application device within the scope of the present invention.

FIG. 3 shows a cutaway side view of a hand-held hemostatic dry powder application device within the scope of the present invention.

FIG. 3A shows a cutaway side view of the dispense flow chamber where gas and powder mix and are conveyed within the scope of the present invention.

FIG. 3B. shows a cutaway side view of the powder pin closing element can be used to meter the powder flow within the scope of the present invention.

FIG. 3C. shows another cutaway side view of the powder pin closing element can be used to meter the powder flow within the scope of the present invention.

FIG. 4 shows a side view of the hand-held hemostatic dry powder delivery device that includes a conduit to equalize gas pressure between the powder chamber and the gas flow path immediately below the powder chamber.

FIG. 5 shows a cutaway frontal view of the hand-held dry powder delivery device shown in FIG. 4 that includes a conduit to equalize gas pressure between the powder chamber and the gas flow path immediately below the powder chamber

DETAILED DESCRIPTION OF THE INVENTION

The invention includes a method and apparatus to deliver dry, flowable hemostatic powder into a gas flow stream by gravity delivery within a body of the apparatus. The hemostatic powder is then carried with the gas out of the apparatus into an elongated delivery tube inserted into a patient. Delivery of the powder into the gas flow stream creates a bolus of powder and gas which becomes more uniformly distributed as it passes through the elongated delivery tube.

The invention also includes a method of delivering dry powder, preferably a dry, flowable hemostatic powder to an internal operation site or wound site of mammals. The term flowable refers to the fact that, if a 15 gram quantity of a specific free-flowing powder is placed in a funnel with 30 degree sloping sides (relative to the central axis of the funnel) that is sealed at its top most diameter, and contains a orifice of dimension 0.150 inches or more at it smallest diameter and this diameter is maintained for a length no more than 2 times the orifice size, the powder will completely flow out the funnel under the force of gravity emptying the funnel and the only gas that flows back into the funnel comes into the lower diameter end of the funnel in the opposite directions as the powder flow. The powder flow may be momentarily interrupted when the gas flows into the funnel. The powder drops in packets, slugs, bolus or other interrupted flow into the mixing (air and powder mix) below the cartridge.

The method further includes the steps of:

(a) extending a distal end of the elongated tubular delivery channel to a position that an emitting opening of said delivery channel is adjacent to said internal operation site or wound site. The term "extending" of the elongated tubular delivery channel is determined by medical procedural demands, and not by technical necessity in the process. The channel (a tube, cannula, etc.) may be extended before attachment to the hand-held device or may be extended after the channel has been attached to the hand-held device. The hand-held device will not be activated until after the channel has been inserted and the channel engaged with the hand-held device. Most preferably, if the tubular delivery channel is to be inserted into the working channel of an endoscope and liquids may be present in this working channel, the channel is to be first attached to the hand-held device and gas flow initiated prior to insertion into the working channel, thus using the positive pressure of the flowing gas to prohibit the possible intrusion of liquid into the lumen of the channel.

The method continues with (b) providing a hand-held application device comprising a handle end and a forward end connected to a proximal end of the elongated tubular delivery channel, generating a conveying gas flow containing pressurized gas to mix with dry powder (preferably a hemostatic powder, but other medicinal powder materials such as antibiotics, scaffolding materials, adhesive, etc.). The gas should of course be medically acceptable within a patient, and likely would be medical grade, pure carbon dioxide or medical grade air provided from a piped source or pressurized gas cannister. The hand-held device further includes a receptor (a seat, a capture support shaped to receive a bottom section of a gravity feeding powder cannister) for a neutral pressure particulate dry hemostatic powder gravity feeding cartridge, and an internal gas flow path from the handle end to the proximal end and passing under the receptor. The cannister is supported and removably secured into the cartridge receptor. The support and securement may be a tight fit, a snap-in connection, a threaded screw-in connection or sliding or gripping lock-unlock connector. The cannister has a opening on a bottom or downward facing end of the cannister, the opening (hole) being large enough to allow powder to flow by gravity downwardly solely by the action of gravity. The size of the hole will depend upon the rate of flow desired and the need to address different gravity flow properties of the powder. Typically, the opening, when cleared of any intended blockage or coverage, should have an internal diameter of at least 4 mm and may be up to 12 mm inside diameter for the opening. The average size of particles in the powder, surface properties and shape of the powder particles shall influence the particle flow properties of the powder out of the cartridge through any funneling shapes in the delivery of the powder into an area where the particles and gas mix. Any optimization of dimensions in the gravity fed path would be modified based on the properties of the particles in the powder.

The process continues by (c) engaging (inserting, connecting, placing, snapping, locking, etc.) the neutral pressure particulate dry hemostatic powder gravity feeding cartridge onto the receptor. It must be clearly understood that the powder flows downwardly by force of gravity, and pressure within the cartridge has no function in delivering powder into the mixing area. This can be understood by analyzing gas pressure during activity of the system. In one embodiment of this invention, the only source of gas entry into the cartridge is upwardly from the tubular delivery channel. The gas flows upwardly into the chamber sporadically and intermittently after powder has been fed out of the cartridge. The removal of powder therefor lowers gas pressure in the cartridge. The reduced pressure is alleviated by intermittent and sporadic bubbling or "burping" of bubbles or boli of gas upward out of the tubular delivery channel. As the gas pressure of these bubbles or boli of gas can never exceed the pressure of flowing gas within the tubular delivery tube, and the pressure in the cartridge is lower than the pressure in the tubular delivery tube when powder is flowing out, the gas pressure in the cartridge will always be at a lower gas pressure than, or at best equal to the pressure in the tubular delivery tube.

In another embodiment of this invention, a gas conduit connects the gas flow channel in the immediate vicinity of where the powder enters the gas flow path to the powder chamber and therefore as powder gravity flows out of the powder chamber, gas may flow through this conduit to replace the volume of gas lost and thus may approximately equalize the gas pressure in the cartridge with that of the gas flow path.

The process then continues by (d) providing a gas conveying tube connected to the flow path at the handle end of the hand-held application device; and (e) providing gas under pressure to the gas conveying tube to cause gas flow through the internal gas flow path and under the receptor. The gas pressure and flow is sufficient to pick up and carry the particles in the powder dropped into that internal gas flow path. That gas pressure, as stated above, can never be lower than the gas pressure in the cartridge, as the only source of additional gas in the cartridge, cannot increase the gas pressure in the cartridge to a pressure higher than that in the internal gas flow path. Therefore, gas pressure in the cartridge can not force powder into the internal gas flow path.

For this reason, in the process (f) only the force of gravity drops the dry hemostatic powder from the opening in the bottom of the cartridge into the internal gas flow path through the receptor.

The gas flowing through the internal gas flow path (g) carries the dropped dry hemostatic powder in the internal gas flow into the proximal end of the elongated tubular delivery channel; and Then (h) delivers the dropped dry hemostatic powder carried in the internal gas flow path to the internal operation site or wound site to assist clotting of blood at the operation site or wound site through the elongated tubular delivery channel.

The method may be continued wherein the dropped dry hemostatic powder is dropped into the internal gas flow while gas pressure above the dry hemostatic powder in the cartridge is lower than gas pressure within the internal gas flow path. As previously described, the gas pressure in the cartridge is reduced by delivering the dropped dry hemostatic powder into the internal gas flow path creating an increased pressure differential between the gas pressure above the dry hemostatic powder in the cartridge and the gas pressure within the internal gas flow path, and intermittently gas in the internal gas flow path will form a bolus of gas and flow up through the dry hemostatic powder in a bottom section of the cartridge to reduce the pressure differential between the gas pressure above the dry hemostatic powder in the cartridge and the gas pressure within the internal gas flow path, without creating a new gas pressure differential between the gas pressure above the dry hemostatic powder in the cartridge and the gas pressure within the internal gas flow path where the gas pressure in the cartridge never exceeds the gas pressure in the internal gas flow path.

The dropped dry hemostatic powder is initially carried in the internal gas flow path at a point below the connector as a first bolus of dry hemostatic powder in gas separated by volumes of gas with a lower concentration of dry hemostatic powder than is present in the first bolus of dry hemostatic powder in gas.

The providing of gas under pressure to the gas conveying tube is initiated by a valve or stopcock that is attached to the hand held device or placed in the tubing between the hand held device and the pressurized gas source. There is a trigger within the handle end of the hand-holdable device which opens and closes an opening for hemostatic powder (by opening and closing the sliding pin) to be gravity fed from the cartridge while there is gas flow from the handle end towards the coupling elements and the distal end of the hand-holdable device. The hemostatic powder drops into flow of gas through the tubing. The drop of hemostatic powder into the tubing is not a steady state process, even if the gas flow is steady. The powder drops in batches or boli into a capture or mixing area directly below or nearly below the cartridge. The gas flow picks up the batches of hemostatic powder, and carries each packet in the gas flow. As elsewhere described herein, these packets get more dispersed within the air flow, and even if a perfect distribution within the gas flow (perfectly dispersed or suspended particles), the degree of dispersion is acceptable for application to a wound site at the distal end of the hand-holdable device, In the method, the first bolus of dry hemostatic powder in gas is believed to at least partially merges with the volumes of gas with a lower concentration of dry hemostatic powder after entering the elongated tubular delivery channel.

The inventions also include an apparatus for delivering dry hemostatic powder to an internal operation site or wound site of mammals including:

- a hand-holdable device having a handle end and a forward end;
- the handle end of the hand-holdable device having a coupling element configured to connect to a gas pressure source and a distal end of the hand-hold-able device having a delivery connector configured to connect to an elongated tubular delivery channel;
- an open passageway comprising an internal gas flow path between the coupling element and the distal end of the hand-holdable device;
- the internal gas flow path intersecting with and connecting to a receptor for a neutral pressure particulate dry hemostatic powder gravity feeding cartridge; and
- a trigger within the handle end of the hand-holdable device which is connected to a moveable stopper (e.g., the sliding pin or plug) that either initiates or ceases the dry hemostatic powder gravity flow into the internal gas flow path.

In the apparatus, the neutral pressure particulate dry hemostatic powder gravity feeding cartridge is dry-flowable powder engaged with the receptor for the neutral pressure particulate dry hemostatic powder gravity feeding cartridge and the receptor is positioned at a relatively upper side of the hand-holdable device.

In the apparatus, a surface of the hand-holdable device opposite to the receptor for the neutral pressure particulate dry hemostatic powder gravity feeding cartridge is a moveable stopper that when open allows gravity feeding of dry hemostatic powder from the neutral pressure particulate dry hemostatic powder gravity feeding cartridge into the internal gas flow path, and when the stopper is closed, prevents gravity feeding of dry hemostatic powder from the neutral pressure particulate dry hemostatic powder gravity feeding cartridge into the internal gas flow path.

In an alternative embodiment the moveable stopper is not needed in the apparatus. Instead the hand-held device can be rotated upon its central gas flowing axis to control powder flow, so that when the cartridge is below the gas flowing axis, gravity holds the powder within the cartridge. When the hand-held device is rotated 180 degrees from this closed position, the cartridge is elevated to allow gravity to feed the powder into the internal gas flow path. When the powder chamber is directly above the internal gas flow path, powder will flow under the force of gravity. As the device is rotated about the central axis of the flow path, the powder chamber will no longer be over the opening leading to the flow path and powder flow will cease. Powder flow can then be reinitiated by reversing this rotation.

In yet another alternative embodiment, the moveable stopper can be configured with a tapered design that extends upward and decreases in diameter as the stopper penetrates into the powder chamber such that the available area for powder flow is dependent on the extent that the trigger controlling the moveable stopper is depressed, thus allowing the metering of the powder flow by the user operating the trigger.

In yet another alternative embodiment, the moveable stopper can be configured with a stepped design that extends upward into the powder chamber with decreasing dimension in stepwise fashion as the stopper penetrates into the powder chamber such that the available area for powder flow is dependent on the extent that the trigger controlling the moveable stopper is depressed, thus allowing the metering of the powder flow by the user operating the trigger.

A greater appreciation of the invention will be gained by reference to the Figures.

FIG. 1 shows a perspective view of a hand-held hemostatic dry powder application device 100 within the scope of the present invention. The device 100 includes a handle end 102 and a delivery end 106. There is a gas entry point 104 on the handle end 102. There is a cartridge connector (acceptor) 110 at an intersection between the handle end 102 and the delivery end 106. A cartridge system 112 which contains the powder to be dispensed is engaged with the cartridge connector 110. The cartridge system 112 is shown with a chamber 114 connected to a chamber collar or sleeve (not shown) which stores the dry hemostatic powder. An interior gas flow path 118 is shown passing through the handle end 102 and the delivery end 106. Transporting gas is introduced at the gas entry point 104, it passes through the interior gas flow path 118 and out through the luer connector 108 and passing into a flexible tubular carrier (not shown) for delivery into the interior of a patient. Trigger 116 controls the gravity flow of powder out of the cartridges and into the interior gas flow path.

FIG. 2 shows an exploded perspective view of a hand-held hemostatic dry powder application device within the scope of the present invention. Component parts include a powder chamber 202, a chamber collar or sleeve 203 that seats into the cartridge connector 211 with an intermediate compression ring or O-ring 221. Gas is introduced into the interior gas flow path 215 through a female luer union 217 and then a male leur union 216 connected to the interior gas flow path 215 shown as tubing, but which also may be a molded chamber. A powder chamber cap 207 is shown that is removed from the powder chamber, in instances where the powder chamber may be packaged separately from the dispenser, and thus allowing the connection of the chamber collar to the cartridge connector 211. A dispense flow chamber 204 is shown below the cartridge connector 211. A closing element, pin or rod 206 is inserted into the bottom of the dispense flow chamber 204 through another O-ring 212 carried in an O-ring container 205. The closing element 206 slides to seat into an opening (not shown) at the bottom of the dispense flow chamber 204. The tube acting as the interior gas flow path 215 is connected through a tube connector 223 to carry gas into the dispense flow chamber 204 into which dry, flowable hemostatic powder is dropped or flows by gravity from the powder chamber 202 into the dispense flow chamber 204 when the pin closing element 206 is withdrawn from the seat to allow powder flow. The gas passing through the interior gas flow path 215 into the dispense flow chamber carries dropped dry, flowable hemostatic powder out through the distal luer connector 214 which is attached to a flexible catheterizing tube (not shown) that directs the carried gas and hemostatic powder to the treatment site. A manual trigger 210 with a biasing spring 222 is used to slide the closing element (e.g., the moveable stopper or closing pin) 206 away from its seat thus allowing for the particles to begin flowing under gravity, when the trigger is depressed. When the trigger is released and under the force of the spring, the closing element 206 slides back and reseats the closing element 206 to cease the flow of particles out of the chamber under gravity.

FIG. 3 shows a cutaway side view of a hand-held hemostatic dry powder application device 300 within the scope of the present invention. Within the device 300 are shown the luer connector 306 to an external gas pressure source (commercial gas line or tank or cartridge containing essentially of inert gas (not shown). The luer connector 306 feeds gas into the interior gas flow path 312 and then out to the luer connector 308. The cartridge 304 sits and is sealingly engaged with a funnel element acting at the cartridge receptor 302 such that when the sliding lock 316 is withdrawn, powder (not shown) in the cartridge 304 drops by gravity into the gas flow path 312. The manually operated trigger 310 operates to lower the sliding lock 316 to open up powder flow under the force of gravity from the cartridge into the interior gas flow path 312. The operation of these elements in allowing gravity to provide powder into the internal gas flow path 312 will be shown in greater detail in FIG. 3A.

FIG. 3A shows a cutaway side view of a cartridge connector 330 to the hand-held hemostatic dry powder application device within the scope of the present invention. The path of gas within the device is from right to left, flowing from the internal gas flow path segment 312*a* to the internal gas flow path segment 312*b*. Shown in this FIG. 3A is the sliding pin 316 in an uppermost position, blocking an opening 318 at the bottom of the funneling slope 314 of the receptor 302 for the powder cartridge (not shown). The tip 322 of the sliding pin 316 contacts the base of the funneling slope to form a particle tight circumferential seal 320 which prevents any gravity flow of powder into the flow path segments 312*a* 312*b*. It is important to note that the tip 322 of the sliding pin (e.g., a stopper) 316 that contacts the base of the funneling slope does not form a gas tight seal with opening 318 at the bottom of the funneling slope 314. Also, it is important to note that in FIG. 3A, the funneling slope 314 is shown at approximately a 30 degree angle relative to the central axis of the receptor 302, however other angles are possible within the scope of the invention, both higher and lower than 30 degrees. Those skilled in the art will realize that practical limits will dictate the choice of angle. For example, if it were to be a requirement that all powder within the cartridge to be dispensed, a 90 degree angle design would not be acceptable as some amount of residual powder would collect in the base of the cartridge as the remaining powder was dispensed. Likewise, if there were a 0 degree angle (effectively making the sloped area a pipe), there would be an increased tendency for particles to jam within the funneling slope (which would then not be sloped). A more generally preferred set of ranges would be between 10-80 degrees, 20-70 degrees, and 30-60 degrees for the gradient in the funneling slope.

FIG. 3B shows a cutaway side view of an alternate sliding pin 336 that can be used in place of sliding pin 316 of FIG. 3A. Element 342 forms and identical type of seal as the tip 322 of the sliding pin 316 which contacts the base of the funneling slope to form a powder seal in FIG. 3A, Thereafter tapering element 343 extends further upward with a steadily decreasing cross-sectional area as one approached the top of the tip. In use, as sliding pin 336 is drawn down to initiate powder flow, the cross-sectional area for powder flow will increase as the pin is further pulled down. Thus, the sliding pin 336 can be used to meter the amount of powder flowing by gravity into the gas stream. As shown in FIG. 3B, element 342 appears as a ledge, however the sliding pin alternatively can have a smooth taper from the sealing position upwards.

FIG. 3C shows a cutaway side view of an alternate sliding pin 356 that can be used in place of sliding pin 316 of FIG. 3A. Element 352 forms and identical type of seal as the tip 322 of the sliding pin 316 which contacts the base of the funneling slope to form a powder seal in FIG. 3A, Thereafter, as shown in FIG. 3C two stepped decreases in diameter exist, 353 and 354 that extend upward. In use, as sliding pin 356 is drawn down to initiate powder flow, the cross-sectional area for powder flow will increase as the different steps of the sliding pin is further pulled down. Thus, the sliding pin 356 can be used to meter the amount of powder flowing by gravity into the gas stream. As shown, sliding pin 356 has 2 stepped decreases but the actual; amount can be greater or lesser.

FIG. 4 shows a perspective view of a hand-held hemostatic dry powder application device 400 within the scope of the present invention. The device 400 includes a handle end 412 and a delivery end 414. There is a gas entry point 406 on the handle end 412. There is a cartridge connector (acceptor) 418 at an intersection between the handle end 412 and the delivery end 414. A cartridge system 404 which contains the flowable powder to be dispensed is engaged with the cartridge connector 418. The cartridge system 404 is shown with a chamber 420 connected to a chamber collar or sleeve (not shown) which stores the dry hemostatic powder. The cartridge system 404 is shown with a gas conduit 402 that connects the top of the cartridge to the internal gas flow path 422 that passes through the handle end 406 to the delivery end 414. Transporting gas is introduced at the gas entry point 406, it passes through the interior gas flow path 422 and out through the luer connector 408 and passing into a flexible tubular carrier (not shown) for delivery into the interior of a patient. Trigger 410 controls the gravity flow of powder out of the cartridges and into the interior gas flow path.

FIG. 5 shows a cutaway frontal view of a hand-held hemostatic dry powder application device 500 within the scope of the present invention, where the cutaway bisects the gas conduit 502, powder chamber 504 and sliding pin 506. The sliding pin 506 in an uppermost position, blocking an opening 508 at the bottom of the funneling slope 510 of the powder chamber 504. The tip 512 of the sliding pin 506 contacts the base of the funneling slope to form a particle and/or gas tight circumferential seal 514 which prevents any gravity flow of powder into the flow path (not shown) and in the case where the seal is gas tight, prevents gas from entering the chamber through the seal area. Gas conduit 502 intersects the internal gas flow path at 516 which is directly inline with the centerline of the sliding pin 506. When trigger 518 is depressed, the sliding pin 506 is lowered such that powder may flow out of the opening 508 of the funneling slope and into the gas flow path. To equalize the lower pressure that is generated when the powder flows out of the powder chamber, gas may flow from the internal gas flow path intersection at 516 through conduit 502 and into the powder chamber 504. Gas pressure in the powder chamber 504 can never exceed gas pressure in the gas flow path at 516, thus powder flow out of the chamber only occurs under the force of gravity.

Any flowable hemostatic powder within a range of size and flow properties may be used. An example of a preferred hemostatic powder is NexStat® Plus topical hemostat powder is an all-natural, plant-based polysaccharide in an easy-to-use applicator ideal for treating bleeding from Endoscopic Sinus Surgeries. NexStat® Plus topical hemostat powder meets ISO 10993 biocompatibility requirements and contains no animal tissue or other bovine agents.

Another hemostatic powder spray is Hemospray® (Cook Medical, Winston-Salem, North Carolina, USA) as a new method and material for managing gastrointestinal bleeding. Hemablock® (HemaBlock LLC, Edina, MN, USA) is another hemostatic powder that can be used in a wide range of sterile and non-sterile procedures. Arista™ AH is a 100% plant based absorbable surgical hemostatic powder derived from purified plant starch. The ability of Arista™ AH (Davol subsidiary of C. R. Bard, Warwick, RI, USA) lies in its microporous polysaccharide hemispheres, a patented blood clotting technology. Other hemostatic powders may be used, with only minor adjustments in opening and tube sizes and variations in air carrying pressure.

Although specific dimensions and materials may be described above, they are specific information within the generic scope of the present invention.

What is claimed:

1. A method of delivering dry hemostatic powder to an internal operation site or wound site of mammals, comprising the steps of:

(a) extending a distal end of an elongated tubular delivery channel to a position that an emitting opening of said delivery channel is adjacent to said internal operation site or wound site;

(b) providing a hand-held application device comprising a handle end and a forward end connected to a proximal end of the elongated tubular delivery channel, generating a conveying gas flow containing pressurized gas to mix with dry powder, a receptor for a neutral pressure particulate dry hemostatic powder gravity feeding cartridge, and an internal gas flow path from the handle end to the proximal end and passing under the receptor;

(c) engaging the neutral pressure particulate dry hemostatic powder gravity feeding cartridge onto the receptor;

(d) providing a gas conveying tube connected to the flow path at the handle end of the hand-held application device;

(e) providing gas under pressure to the gas conveying tube to increase gas pressure and cause gas flow through the internal gas flow path and under the receptor;

(f) gravity dropping the dry hemostatic powder from a bottom of the cartridge into the internal gas flow path through the receptor, with pressure within the cartridge having no function in delivering powder into the mixing area;

(g) carrying the dropped dry hemostatic powder in the internal gas flow into the proximal end of the elongated tubular delivery channel; and (h) delivering the dropped dry hemostatic powder carried in the internal gas flow path to the internal operation site or wound site to assist clotting of blood at the operation site or wound site through the elongated tubular delivery channel.

2. The method of claim 1 wherein the dropped dry hemostatic powder is dropped into the internal gas flow while gas pressure above the dry hemostatic powder in the cartridge is lower than gas pressure within the internal gas flow path.

3. The method of claim 2 wherein the gas pressure in the cartridge is reduced by delivering the dropped dry hemostatic powder into the internal gas flow path creating an increased pressure differential between the gas pressure above the dry hemostatic powder in the cartridge and the gas pressure within the internal gas flow path, and intermittently gas in the internal gas flow path will form a bolus of gas and flow up through the dry hemostatic powder in a bottom section of the cartridge to reduce the pressure differential between the gas pressure above the dry hemostatic powder in the cartridge and the gas pressure within the internal gas flow path, without creating a new gas pressure differential between the gas pressure above the dry hemostatic powder in the cartridge and the gas pressure within the internal gas flow path where the gas pressure in the cartridge never exceeds the gas pressure in the internal gas flow path.

4. The method of claim 1 wherein dropped dry hemostatic powder is initially carried in the internal gas flow path at a point below where the gas conveying tube is connected to the flow path as a first bolus of dry hemostatic powder in air separated by volumes of air with a lower concentration of dry hemostatic powder than is present in the first bolus of dry hemostatic powder in air.

5. The method of claim 2 wherein dropped dry hemostatic powder is initially carried in the internal gas flow path at a point below where the gas conveying tube is connected to the flow path as a first bolus of dry hemostatic powder in air separated by volumes of air with a lower concentration of dry hemostatic powder than is present in the first bolus of dry hemostatic powder in air.

6. The method of claim 3 wherein dropped dry hemostatic powder is initially carried in the internal gas flow path at a point below where the gas conveying tube is connected to the flow path as a first bolus of dry hemostatic powder in air separated by volumes of air with a lower concentration of dry hemostatic powder than is present in the first bolus of dry hemostatic powder in air.

7. The method of claim 1 wherein providing gas under pressure to the gas conveying tube is initiated by a stopcock or valve on the hand-held application device that allows pressure to flow from a gas cylinder or gas pressure line into internal gas flow path in a vector from the handle end to the elongated tubular delivery channel.

8. The method of claim 5 wherein providing gas under pressure to the gas conveying tube is initiated by a stopcock or valve on the hand-held application device that allows pressure to flow from a gas cylinder or gas pressure line into internal gas flow path in a vector from the handle end to the elongated tubular delivery channel.

9. The method of claim 6 wherein providing gas under pressure to the gas conveying tube is initiated by a stopcock or valve on the hand-held application device that allows pressure to flow from a gas cylinder or gas pressure line into internal gas flow path in a vector from the handle end to the elongated tubular delivery channel.

10. The method of claim 9 wherein the first bolus of dry hemostatic powder in air at least partially merges with the volumes of air with a lower concentration of dry hemostatic powder after entering the elongated tubular delivery channel.

11. The method of claim 1 wherein pressure is maintained at approximately equal or less than levels between the cartridge and the internal gas flow path by a gas conductive tube between the cartridge and the internal gas flow path.

12. A method of delivering dry hemostatic powder to an internal operation site or wound site of mammals, comprising the steps of:

(a) extending a distal end of an elongated tubular delivery channel to a position that an emitting opening of said delivery channel is adjacent to said internal operation site or wound site;

(b) providing a hand-held application device comprising a handle end and a forward end connected to a proximal end of the elongated tubular delivery channel, generating a conveying gas flow containing pressurized gas to mix with dry powder, a receptor for a neutral pressure particulate dry hemostatic powder gravity feeding cartridge, and an internal gas flow path from the handle end to the proximal end and passing under the receptor;

(c) engaging the neutral pressure particulate dry hemostatic powder gravity feeding cartridge onto the receptor;

(d) providing a gas conveying tube connected to the flow path at the handle end of the hand-held application device;

(e) providing gas under pressure to the gas conveying tube to increase gas pressure and cause gas flow through the internal gas flow path and under the receptor;

(f) solely gravity dropping the dry hemostatic powder from a bottom of the cartridge into the internal gas flow path through the receptor;

(g) carrying the dropped dry hemostatic powder in the internal gas flow into the proximal end of the elongated tubular delivery channel; and (h) delivering the dropped dry hemostatic powder carried in the internal gas flow path to the internal operation site or wound site to assist clotting of blood at the operation site or wound site through the elongated tubular delivery channel, wherein the dropped dry hemostatic powder is dropped into the internal gas flow solely by gravity while gas pressure above the dry hemostatic powder in the cartridge is lower than gas pressure within the internal gas flow path, and wherein the gas pressure in the cartridge is reduced by delivering the dropped dry hemostatic powder into the internal gas flow path, the dropped dry hemostatic powder creating an increased pressure differential between gas pressure above the dry hemostatic powder in the cartridge and gas pressure within the internal gas flow path, and intermittently gas in the internal gas flow path will form a bolus of gas and flow up through the dry hemostatic powder in a bottom section of the cartridge to reduce the pressure differential between the gas pressure above the dry hemostatic powder in the cartridge and the gas pressure within the internal gas flow path, without creating a new gas pressure differential between the gas pressure above the dry hemostatic powder in the cartridge and the gas pressure within the internal gas flow path where the gas pressure in the cartridge never exceeds the gas pressure in the internal gas flow path.

13. The method of claim 12 wherein dropped dry hemostatic powder is initially carried in the internal gas flow path at a point below the connector as a first bolus of dry hemostatic powder in air separated by volumes of air between at least one subsequent additional bolus of dry hemostatic powder with a lower concentration of dry hemostatic powder than is present in the first bolus of dry hemostatic powder in air.

14. The method of claim 12 wherein dropped dry hemostatic powder is initially carried in the internal gas flow path at a point below the connector as a first bolus of dry hemostatic powder in air separated by volumes of air with a lower concentration of dry hemostatic powder than is present in the first bolus of dry hemostatic powder in air.

15. A method of delivering dry hemostatic powder to an internal operation site or wound site of mammals, comprising the steps of:
  (a) extending a distal end of an elongated tubular delivery channel to a position that an emitting opening of said delivery channel is adjacent to said internal operation site or wound site;
  (b) providing a hand-held application device comprising a handle end and a forward end connected to a proximal end of the elongated tubular delivery channel, generating a conveying gas flow containing pressurized gas to mix with dry powder, a receptor for a neutral pressure particulate dry hemostatic powder gravity feeding cartridge, and an internal gas flow path from the handle end to the proximal end and passing under the receptor;
  (c) engaging the neutral pressure particulate dry hemostatic powder gravity feeding cartridge onto the receptor;
  (d) providing a gas conveying tube connected to the flow path at the handle end of the hand-held application device;
  (e) providing gas under pressure to the gas conveying tube to increase gas pressure and cause gas flow through the internal gas flow path and under the receptor;
  (f) combining the dry hemostatic powder from a bottom of the cartridge into the internal gas flow path through the receptor by force consisting essentially of gravity;
  (g) carrying the dropped dry hemostatic powder in the internal gas flow into the proximal end of the elongated tubular delivery channel; and
  (h) delivering the dropped dry hemostatic powder carried in the internal gas flow path to the internal operation site or wound site to assist clotting of blood at the operation site or wound site through the elongated tubular delivery channel.

16. The method of claim 15 wherein the dropped dry hemostatic powder is dropped into the internal gas flow while gas pressure above the dry hemostatic powder in the cartridge is lower than gas pressure within the internal gas flow path.

17. The method of claim 16 wherein the gas pressure in the cartridge is reduced by delivering the dropped dry hemostatic powder into the internal gas flow path creating an increased pressure differential between the gas pressure above the dry hemostatic powder in the cartridge and the gas pressure within the internal gas flow path, and intermittently gas in the internal gas flow path will form a bolus of gas and flow up through the dry hemostatic powder in a bottom section of the cartridge to reduce the pressure differential between the gas pressure above the dry hemostatic powder in the cartridge and the gas pressure within the internal gas flow path, without creating a new gas pressure differential between the gas pressure above the dry hemostatic powder in the cartridge and the gas pressure within the internal gas flow path where the gas pressure in the cartridge never exceeds the gas pressure in the internal gas flow path.

18. The method of claim 15 wherein dropped dry hemostatic powder is initially carried in the internal gas flow path at a point below where the gas conveying tube is connected to the flow path as a first bolus of dry hemostatic powder in air separated by volumes of air with a lower concentration of dry hemostatic powder than is present in the first bolus of dry hemostatic powder in air.

19. The method of claim 15 wherein providing gas under pressure to the gas conveying tube is initiated by a stopcock or valve on the hand-held application device that allows pressure to flow from a gas cylinder or gas pressure line into internal gas flow path in a vector from the handle end to the elongated tubular delivery channel.

* * * * *